United States Patent
Glaug et al.

(10) Patent No.: US 12,239,514 B2
(45) Date of Patent: Mar. 4, 2025

(54) ABSORBENT ARTICLE WITH IMPROVED FLUID CONTAINMENT AND COMFORT

(71) Applicant: Irving Consumer Products Limited, Dieppe (CA)

(72) Inventors: Frank Glaug, Chester Springs, PA (US); Gabriella Makarious, Shediac (CA); James DeFelice, Rogers, AR (US)

(73) Assignee: Irving Consumer Products Limited, Dieppe (CA)

( * ) Notice: Subject to any disclaimer, the term of this patent is extended or adjusted under 35 U.S.C. 154(b) by 973 days.

(21) Appl. No.: 17/313,492

(22) Filed: May 6, 2021

(65) Prior Publication Data

US 2021/0346210 A1 Nov. 11, 2021

Related U.S. Application Data

(60) Provisional application No. 63/021,903, filed on May 8, 2020.

(51) Int. Cl.
*A61F 13/49* (2006.01)
*A61F 13/539* (2006.01)
*A61F 13/15* (2006.01)

(52) U.S. Cl.
CPC ............ *A61F 13/49* (2013.01); *A61F 13/539* (2013.01); *A61F 2013/15959* (2013.01); *A61F 2013/15967* (2013.01); *A61F 2013/49092* (2013.01); *A61F 2013/53908* (2013.01); *A61F 2013/53991* (2013.01)

(58) Field of Classification Search
CPC ................... A61F 13/49; A61F 13/539; A61F 2013/15959; A61F 2013/15967; A61F 2013/53908; A61F 2013/53991; A61F 2013/49092; A61F 2013/49093; A61F 2013/4944; A61F 2013/4948; A61F 13/49413; A61F 13/4942; A61F 13/49446
See application file for complete search history.

(56) References Cited

U.S. PATENT DOCUMENTS

| 3,995,637 A | 12/1976 | Schaar |
| 5,064,421 A | 11/1991 | Tracy |
| 5,234,422 A | 8/1993 | Sneller et al. |
| 5,308,346 A | 5/1994 | Sneller et al. |
| 5,460,622 A | 10/1995 | Dragoo et al. |
| 5,490,847 A | 2/1996 | Correa et al. |

(Continued)

FOREIGN PATENT DOCUMENTS

EP 998891 A2 5/2000

OTHER PUBLICATIONS

Roe et al. United States Statutory Invention Registration. Reg. Number: H1630. (Year: 1997).

*Primary Examiner* — Susan S Su
(74) *Attorney, Agent, or Firm* — SMART & BIGGAR LP

(57) ABSTRACT

The present invention relates generally to absorbent products, and, more particularly, to disposable absorbent articles that provide improvements in the containment of bodily fluid secretions. The fluid containment improvements are the result of adding gasketing barriers to standing leg cuffs of various absorbent articles. Adding gasketing barriers to the standing leg cuffs will decrease fluid leakage at the leg and crotch area of the user and will improve the comfort of the user.

18 Claims, 12 Drawing Sheets

(56) References Cited

U.S. PATENT DOCUMENTS

| | | | |
|---|---|---|---|
| 5,558,660 A * | 9/1996 | Dreier | A61F 13/49413 |
| | | | 604/385.19 |
| 5,601,545 A | 2/1997 | Glaug et al. | |
| 5,797,824 A | 8/1998 | Tracy | |
| 5,827,259 A | 10/1998 | Laux et al. | |
| 6,245,051 B1 | 6/2001 | Zenker et al. | |
| 6,334,858 B1 | 1/2002 | Ronnberg et al. | |
| 6,425,889 B1 | 7/2002 | Kitaoka et al. | |
| 6,664,440 B2 | 12/2003 | Kawamura et al. | |
| 6,881,207 B1 | 4/2005 | Tracy | |
| 9,044,358 B2 | 6/2015 | Nakajima et al. | |
| 10,524,962 B2 | 1/2020 | Raycheck et al. | |
| 10,709,618 B2 | 7/2020 | Bishop et al. | |
| 2003/0050616 A1 | 3/2003 | Reynolds et al. | |
| 2006/0058767 A1 | 3/2006 | Zhang et al. | |
| 2008/0312622 A1 | 12/2008 | Hundorf et al. | |
| 2012/0330260 A1* | 12/2012 | Bishop | A61F 13/53743 |
| | | | 604/378 |
| 2017/0239104 A1* | 8/2017 | Jang | A61F 13/49001 |
| 2018/0104116 A1* | 4/2018 | Bishop | A61F 13/49466 |
| 2019/0358097 A1 | 11/2019 | Chmielewski et al. | |
| 2021/0346210 A1 | 11/2021 | Glaug et al. | |

* cited by examiner

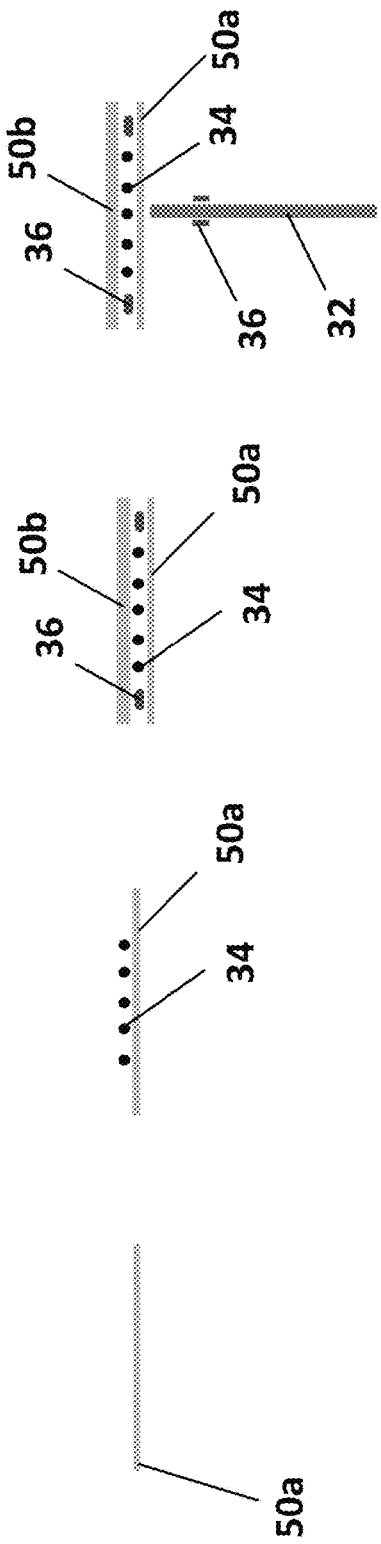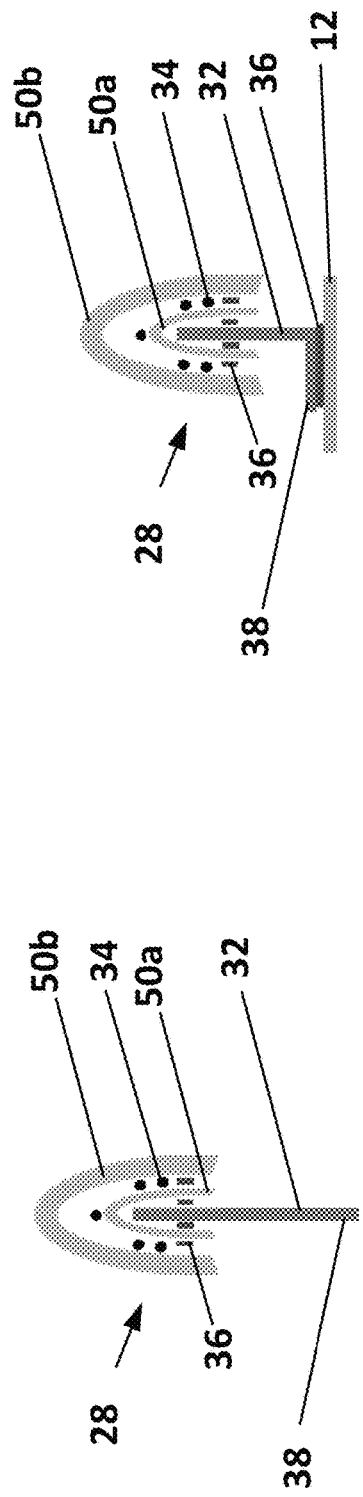

ABSORBENT ARTICLE WITH IMPROVED FLUID CONTAINMENT AND COMFORT

CROSS-REFERENCE TO RELATED APPLICATIONS

This application claims the benefit of U.S. Provisional Application No. 63/021,903 filed on May 8, 2020, which is incorporated by reference herein in its entirety.

FIELD

The described embodiments relate generally to disposable absorbent articles, and, more particularly, to a disposable absorbent diapers and pants (adult and child) and the like.

BACKGROUND

The following is not an admission that anything discussed below is part of the prior art or part of the common general knowledge of a person skilled in the art.

There are several types of commercially available products for the absorption of bodily fluids. Such absorbent products are available in different types, designs, and dimensions, each one having one or more unique features. For example, training pants, baby diapers, adult diapers, adult pants, and incontinence guards are products designed for the containment of urine and excrement. There are other types of disposable absorbent articles, such as feminine hygiene products (e.g., heavy and light incontinence pads, pantyliners, etc.) that are designed to contain and absorb urine and/or menses by female wearers.

Absorbent products typically include a topsheet facing the body of the wearer, a backsheet facing the garment of the wearer and an absorbent core located between the topsheet and backsheet. In some cases, acquisition distribution layers (ADL) are provided between the topsheet and the absorbent core. ADLs help in the fast absorption and distribution of bodily fluids. In addition, standing leg cuffs may be provided at each side of the absorbent core, in the longitudinal direction of the product, to help prevent side leakage of the bodily fluids within the crotch and leg regions of the body. The leg and waist openings of the product are gathered with elastomeric material(s) to help support the product against the skin of the user and reduce leakage of the bodily fluids at the waist and legs.

While these types of absorbent articles may collect body fluid discharge as intended, many of these products tend to leak when exposed to higher fluid volumes, longer periods of wear, and increased stress conditions when the user is active. This leakage may lead to frequent changing of the user's outer garments, bed sheets, baby seat covers, etc. In addition to the nuisance of cleaning-up and washing clothes, there is always the embarrassment to both the user and caretaker of soiled clothing and surroundings.

Current commercially available absorbent products are generally insufficient in providing fully effective fluid barrier that prevents fluid leakage, especially when the product is saturated with fluid and is under stress. Some commercial absorbent products provide standing leg cuffs for limited leakage protection in the crotch and leg areas. In addition, the standing leg cuffs are made of thin nonwoven materials, that are elongated with elastics, in order to gather the material. The combination of elastic materials that are sandwiched in between thin materials, under high elastic tension, may cause it to be rough and scratchy. This may result in red marking or irritation to the skin, especially when the material becomes wet, and friction is caused by the rubbing the material against the body when the user is active. In addition, the combination of elastic materials sandwiched in between thin materials will create a corrugated configuration or micro-gaps along the top edge of the standing leg cuff. These corrugations or micro-gaps may allow more fluid to pass through it, especially when fluid is directed at the standing leg cuff, causing leakage. This is especially prevalent with male users, where the penis maybe near the standing leg cuff and pointing right at the gasketing area.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with one aspect of this disclosure, which may be used alone or in combination with any other aspect, there is provided an absorbent article having a front edge, a back edge, and two longitudinally extending side edges, the absorbent article comprising:
  a topsheet, the topsheet being liquid pervious;
  a backsheet coupled to the topsheet, the backsheet being liquid impervious;
  an absorbent core disposed between the topsheet and backsheet, the absorbent core containing at least one absorbent material;
  an acquisition distribution layer disposed between a bottom side of the topsheet and a top side of the absorbent core; and
  first and second standing leg cuffs, each standing leg cuff includes:
    a cuff web having a base and a top with a first side and an opposed second side extending between the base and the top, the base coupled to the topsheet;
    one or more elastics coupled adjacent to the top of the cuff web;
    a gasketing barrier coupled to the second side of the cuff web,
wherein the cuff web is made of a first material, the gasketing barrier is made of a second material, and the first material is different than the second material.

In some embodiments, the second material may be softer than the first material as measured by any one of the SGS TS7 test and the SGS TS750 test.

In some embodiments, the second material may be softer than the first material as measured by the SGS softness index.

In some embodiments, the gasketing barrier may extend from the base to the top of the cuff web.

In some embodiments, the top of the cuff web may comprise a folded portion, the folded portion for covering the one or more elastics.

In some embodiments, the first material may have a basis weight in the range of about 10 gsm to about 15 gsm.

In some embodiments, the second material may have a basis weight in the range of about 20 gsm to about 25 gsm.

In some embodiments, each gasketing barrier may surround the top of the corresponding cuff web.

In some embodiments, in each standing leg cuff, the elastics may be tensioned to lift the top of the standing leg cuff.

In some embodiments, the bases of the standing leg cuffs may be coupled to the topsheet with at least one of an adhesive and ultrasonic bonding.

In some embodiments, each gasketing barrier may be coupled to each cuff web by at least one of an adhesive and ultrasonic bonding.

In some embodiments, at least one of the cuff web and the gasketing barrier may comprise at least one of a hydrophobic spunbond-meltblown-spunbond nonwoven, a poly film, a breathable film, a poly laminate, a carded web nonwoven, a through-air carded nonwoven, and a hydrophobic spunlaced nonwoven.

In some embodiments, the cuff web may comprise a spunbond-meltblown-spunbond nonwoven and the gasketing barrier may comprise a carded web nonwoven.

In some embodiments, the carded web may comprise bicomponent fibers and polypropylene.

In some embodiments, each standing leg cuff may be assembled with a transverse outboard portion of the topsheet and a transverse inboard portion of a side sheet.

In some embodiments, at least some of the elastics may be positioned between the transverse outboard portion of the topsheet and the transverse inboard portion of the side sheet.

In accordance with one aspect of this disclosure, which may be used alone or in combination with any other aspect, there is provided an absorbent article having a front edge, a back edge, and two longitudinally extending side edges, the absorbent article comprising:
  a topsheet, the topsheet being liquid pervious;
  a backsheet coupled to the topsheet, the backsheet being liquid impervious;
  an absorbent core disposed between the topsheet and backsheet, the absorbent core containing at least one absorbent material;
  an acquisition distribution layer disposed between a bottom side of the topsheet and a top side of the absorbent core; and
  first and second standing leg cuffs, each standing leg cuff includes:
    a base coupled to the topsheet;
    one or more elastics coupled adjacent to a top of the standing leg cuff;
    a gasketing barrier coupled to the top of the standing leg cuff,
  wherein at least one of the elastics is covered by the gasketing barrier.

In some embodiments, each gasketing barrier may surround the top of the corresponding web.

In some embodiments, in each standing leg cuff, the elastics may be tensioned to lift the top of the standing leg cuff.

In some embodiments, each standing leg cuff may be assembled with a transverse outboard portion of the topsheet and a transverse inboard portion of a side sheet.

In some embodiments, at least some of the elastics may be positioned between the transverse outboard portion of the topsheet and the transverse inboard portion of the side sheet.

In some embodiments, the gasketing barrier may extend from the base to the top of the cuff web.

In some embodiments, the top of the cuff web may comprise a folded portion, the folded portion for covering the one or more elastics.

In some embodiments, the web may comprise a web material, the gasketing barriers may comprise a gasketing barrier material and the web material and the gasketing barrier material may be different materials.

In some embodiments, the gasketing barrier material may be softer than the web material as measured by any one of the SGS TS7 test and the SGS TS750 test.

In some embodiments, the gasketing barrier material may be softer than the web material as measured by the SGS softness index.

In some embodiments, the web material may have a basis weight in the range of about 10 gsm to about 15 gsm.

In some embodiments, the gasketing barrier material may have a basis weight in the range of about 20 gsm to about 25 gsm.

In some embodiments, the bases of the standing leg cuffs may be coupled to the topsheet with at least one of an adhesive and ultrasonic bonding.

In some embodiments, each gasketing barrier may be coupled to each web by at least one of an adhesive and ultrasonic bonding.

In some embodiments, at least one of the web and the gasketing barrier may comprise at least one of a hydrophobic spunbond-meltblown-spunbond nonwoven, a poly film, a breathable film, a poly laminate, a carded web nonwoven, a through-air carded nonwoven, and a hydrophobic spunlaced nonwoven.

In some embodiments, the cuff web may comprise a spunbond-meltblown-spunbond nonwoven and the gasketing barrier may comprise a carded web nonwoven.

In some embodiments, the carded web may comprise bicomponent fibers and polypropylene.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIGS. 5A-5F show a process for assembling a standing leg cuff on the disposable absorbent article of FIG. 4 in accordance with another example embodiment;

Figure 1:
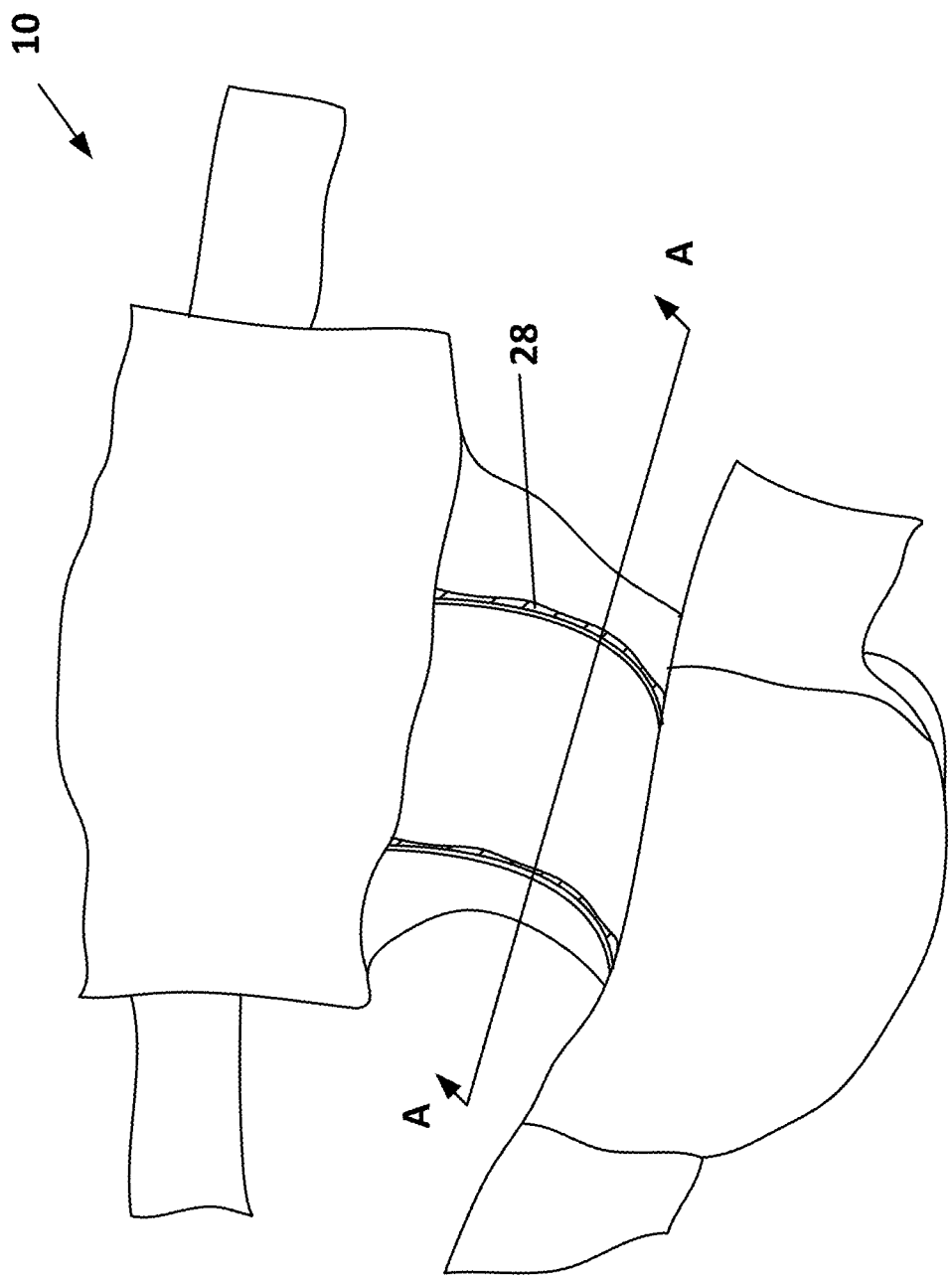
FIG. 1 shows a perspective view of a disposable absorbent article in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

As used herein and in the claims, two or more parts are said to be "coupled", "connected", "attached", or "fastened" (which may all be used interchangeably) where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. None of the terms "coupled", "connected", "attached", and "fastened" distinguish the manner in which two or more parts are joined together. For example, two or more parts may be "coupled", "connected", "attached" or "fastened" by bonding them together with an ultrasonic or heat bond or other technique that does not require a bonding agent, with a bonding agent such as an adhesive, through mechanical bonding, with a mechanical fastener, or in any other manner.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein.

Also, the description is not to be considered as limiting the scope of the example embodiments described herein.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Disposable absorbent articles, such as disposable undergarments, pants, diapers, other garments, have either a closed (e.g., pants) or open (e.g., diapers) product chassis, with an absorbent core system located between two substrate layers. The first substrate layer is on the inside of the article, often referred to as a topsheet, and the second substrate is on the outside of the article, often referred to as a backsheet. The absorbent core system often contains a mixture of pulp and super absorbent polymer (SAP). In some cases, absorbent cores have been designed to be thinner to improve the comfort of users and to provide a better product fit. One process of making the absorbent core thinner is to increase the quantity of SAP and decrease the quantity of pulp. However, SAP requires a certain amount of void volume to properly absorb liquids. Increasing the SAP relative to the pulp may result in fluid that is not absorbed rapidly, often referred to as free fluid. Accordingly, an acquisition distribution layer (ADL) may be added on top of the absorbent core. The ADL can provide the void volume needed to absorb the free fluid the SAP inside the absorbent core could not rapidly absorb. In addition to the ADL, a standing leg cuff is provided along each longitudinal side of the absorbent core, thereby reducing fluid leakage along the crotch and leg areas. In various embodiments, the standing leg cuffs may be positioned above the absorbent core or transversely outboard of the absorbent core.

Figure 2:
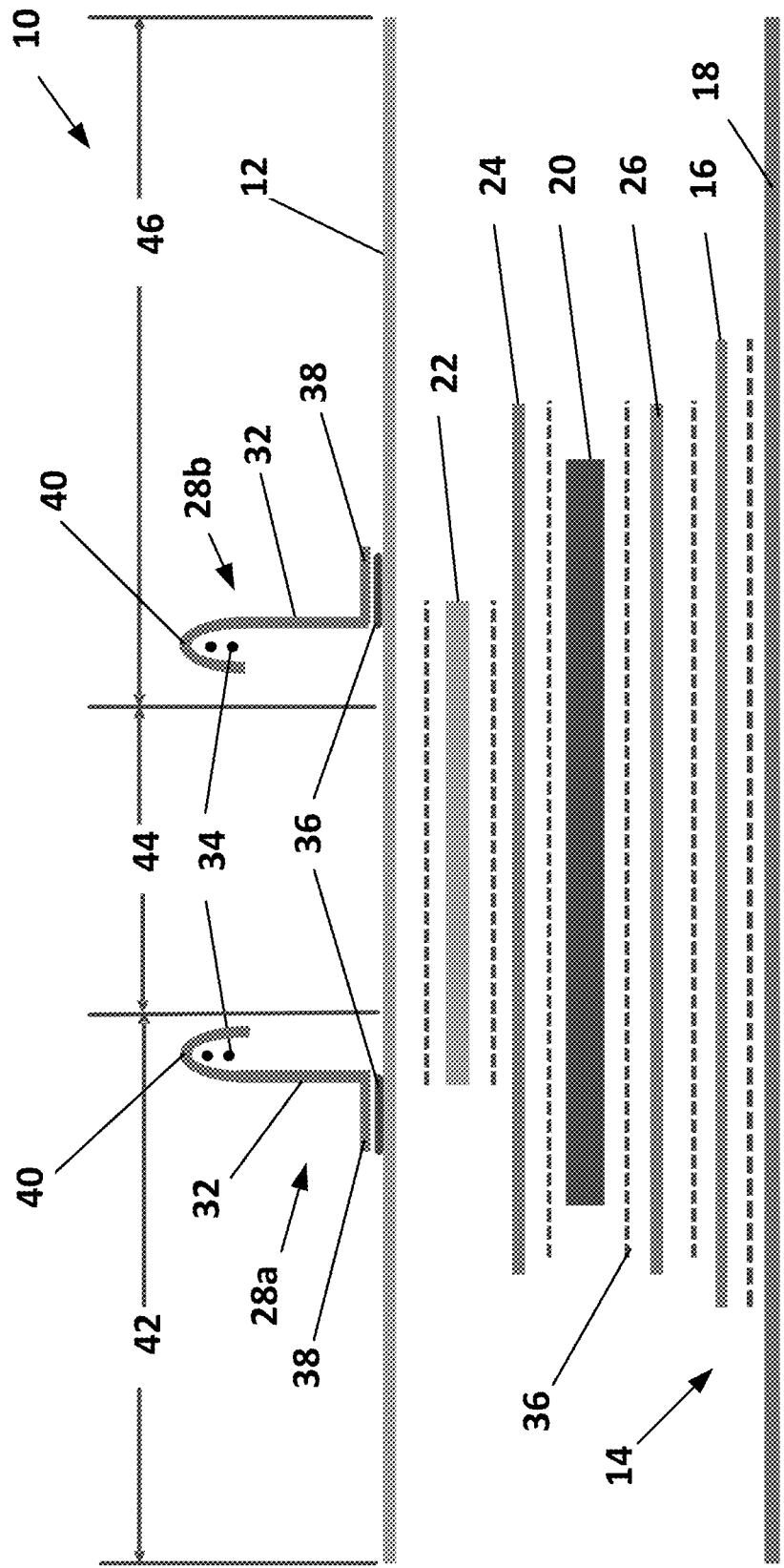
FIG. 2 shows a cross-sectional view of the disposable absorbent article of FIG. 1 along the line A-A.
Figure 3:
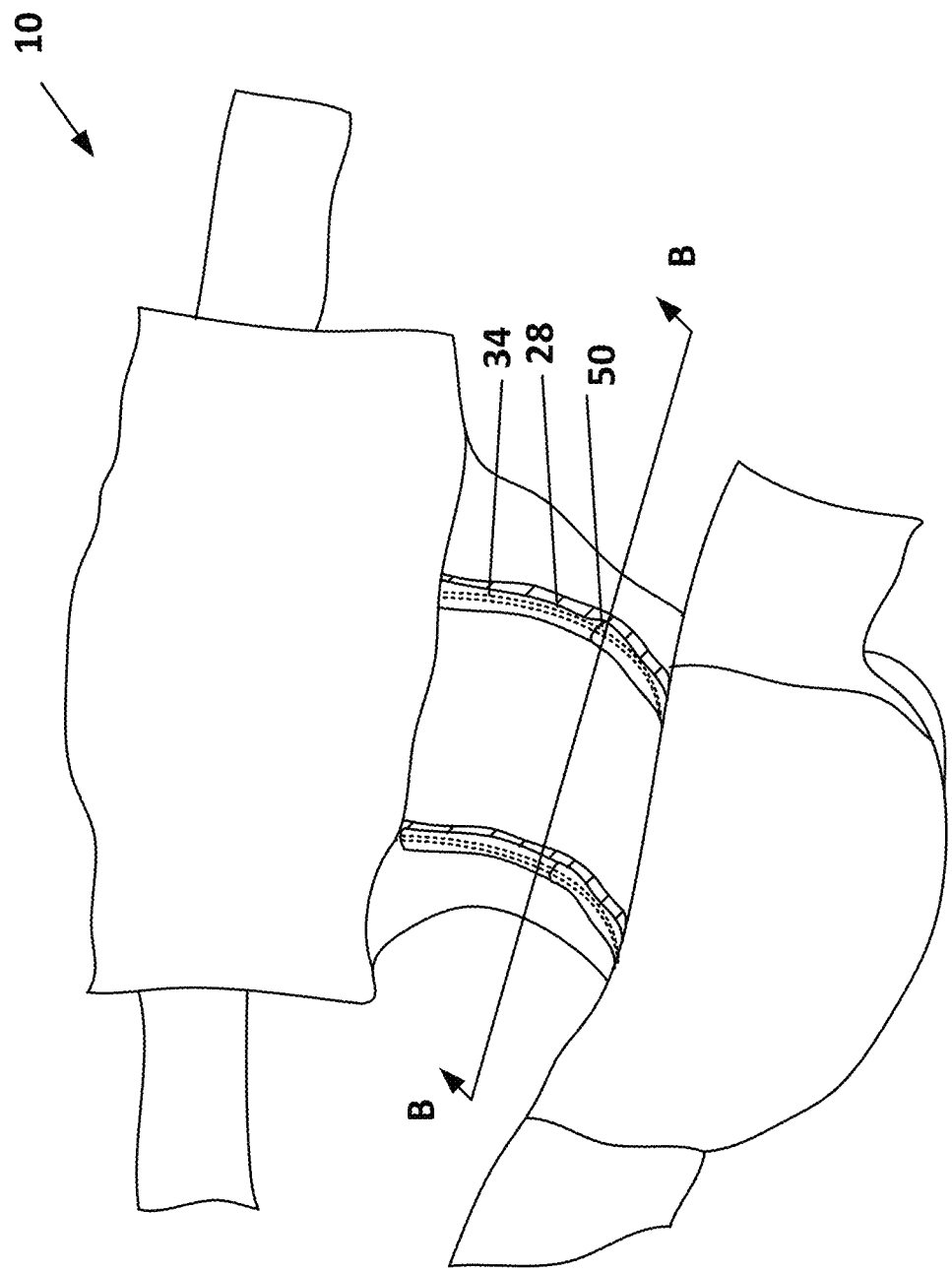
FIG. 3 shows a perspective view of a disposable absorbent article having a gasketing barrier in accordance with another example embodiment.

Referring to FIGS. 1-2, shown therein is an example embodiment of a disposable absorbent article 10. The article 10 has a topsheet 12 and a backsheet 14. In this example embodiment, the backsheet 14 is formed of two layers: a poly barrier 16 and a nonwoven backsheet 18. An absorbent core 20 is disposed between the topsheet 12 and the backsheet 14. An acquisition distribution layer 22 is positioned between the topsheet 12 and the absorbent core 16. In this example embodiment, the absorbent core 20 is positioned between a top core wrap 24 and a bottom core wrap 26. Either or both of the top and bottom core wraps 24, 26 may be a tissue or a nonwoven web. The top and bottom core wraps may fully or partially cover, surround, or wrap around all or part of the absorbent core 20.

In the example of FIGS. 1-2, the article 10 includes a first standing leg cuff 28a and a second standing leg cuff 28b, referred to together as standing leg cuffs 28. The standing leg cuffs 28 include a cuff web 32 and one or more elastic strands 34. In some embodiments, the standing leg cuffs may include a plurality of elastic strands 34. As exemplified, the standing leg cuffs are coupled to the topsheet 12 by one or more bonds 36. The bond 36 may be any bond type capable of securing various components of the article 10 to another component of the article 10. For example, as illustrated, the bonds 36 are adhesive. In some embodiments, the bonds 36 may be ultrasonic bonds. In some embodiments, some of the bonds 36 may be adhesive and some may be ultrasonic.

The various layers of the article 10 may be formed of different materials. The topsheet 12 is at least partially liquid pervious. For example, the topsheet 12 may be a hydrophilic nonwoven web. The ADL 22 may be made of a high loft carded nonwoven. In some embodiments, the ADL 22 may include or be formed of an apertured poly film. The apertures of the apertured poly film may be 3-dimensional. The absorbent core 20 may be formed of a single layer or a dual layer. In some embodiments, the absorbent core 20 may be made of an airlaid material. The absorbent core 20 has one or more absorbent materials.

In some embodiments, the absorbent core 20 may have a plurality of absorbent materials. The absorbent core 20 may be made of pulp, SAP, or a blend of pulp and SAP. In FIGS. 1-2, the absorbent core 20 includes a single layer containing a blend of pulp and SAP. The absorbent material in the absorbent core may be a single pulp material or a plurality of pulp materials. For example, the absorbent material may include one or more of the following: rayon fibers, cotton fibers, bamboo fibers, soft pine, eucalyptus fibers, superabsorbent polymer particles, superabsorbent polymer fibers, peat moss, cross-linked cellulose fibers, cellulose acetate, polypropylene tow, polymer fibers, surfactant treated nonwovens, binder fibers, linen fibers, hemp fibers, ramie fibers, jute fibers, natural cellulose fibers, miscanthus pulp fibers, sponges, absorbent foams, etc.

As described above, the backsheet 14 may be a laminate that includes both the poly barrier 16 and the nonwoven backsheet 18. The poly barrier 16 is typically fluid impervious. In some embodiments, the poly barrier 16 may be a poly film. In some embodiments, the poly barrier 16 may be a breathable poly material, such as a microporous film. The backsheet 14 and/or the absorbent core 20 may include a poly laminate whereby the poly film is extruded onto the nonwoven web.

In some embodiments, at least a portion of the topsheet 12 may be treated with a surfactant. The surfactant renders the topsheet 12 hydrophilic, thereby facilitating fluid flow to areas that have been surfactant treated. For example, referring still to FIGS. 1-2, the topsheet 12 has three zones: a left zone 42, a middle zone 44, and a right zone 46. In some embodiments, the middle zone 44 may be treated with the surfactant, such that the middle zone 44 has increased hydrophilicity relative to the left and right zones 42, 46. In some embodiments, the topsheet 12 may be hydrophobic. Accordingly, the topsheet 12 may be strategically treated by the surfactant to improve the fluid flow from the topsheet 12 to the ADL 22. In some embodiments, the middle zone 44 may be processed to allow fluids to flow through. For example, the portion of the topsheet 12 in the middle zone 44 may be perforated or formed of a porous material to allow fluid to flow more easily through the topsheet 12.

As exemplified in FIGS. 1-2, the base 38 of each standing leg cuff 28 is coupled to the topsheet 12 within the left zone 42 and right zone 46 through a bond 36. In some embodiments, the standing leg cuffs 28 may be coupled to the topsheet 12 adjacent the transverse inboard edges of the left and right zones 42, 46. By coupling the base 38 of the standing leg cuffs 28 along these edges, the risk of fluid wicking underneath the standing leg cuffs 28 is decreased. To achieve the standing function of each standing leg cuff 28, one or more elastics 34 are tensioned or elongated and coupled to the cuff web 32 adjacent to its top 40. The top 40 may be the top edge of the standing leg cuff 28 or may encompass a top region of the standing leg cuff 28 that does not include the base 38. In other words, the top region 40 is distal to the base 38 of the standing leg cuff 28. The cuff web 32 is then folded over and coupled to itself to cover the elastics 34. The cuff web 32 may be closed over the elastics 34 by any means known in the art, such as with an adhesive, mechanical fastening or by ultrasonic bonding. By folding the cuff web 32 over the elongated elastics 34, the standing leg cuff 28 is lifted away from the topsheet and may extend upwardly from the topsheet 12, thereby allowing the standing leg cuffs 28 to come into contact with the body of a user when in use.

Gasketing Barrier

One of the most important functions of disposable absorbent articles is to absorb bodily fluids quickly and adequately, in order to prevent fluid leakage outside of the product. In some cases, the absorbent cores may be overwhelmed in certain regions with the high volumes of fluid that is emitted upon them in a short period of time. As described above, some absorbent core designs have been thinned by increasing the ratio of SAP to pulp in the composition of the absorbent core. SAP takes longer to absorb liquid than pulp, thereby occasionally resulting in free fluid that is not absorbed immediately by the absorbent core. In addition, the absorbent core, or a portion of it, can become saturated with fluid, which slows down the flow of fluid into the core. The possibility of free fluid flowing within the product and the inability of the absorbent core to absorb all fluid at once results in a need for an improved fluid barrier and containment system.

In an example embodiment, there is provided an absorbent article with improved leakage protection and comfort, as shown in FIGS. 3-11. In the example embodiments, the absorbent article 10 includes standing leg cuffs 28, each having a gasketing barrier 50 at the top 40 of the standing leg cuff 28. The gasketing barrier 50 is coupled to, or near to, the standing leg cuffs 28, thereby providing a more efficient means of containing the fluid and preventing the fluid from leaking out of the product. Reducing the leakage thus provides improved absorbency performance during use.

In some embodiments, the gasketing barriers 50 may be formed of a soft and lofty nonwoven material. For example, the soft and lofty nonwoven material of the gasketing barriers 50 is softer than one or more of the topsheet 12 and the cuff web 32. The soft gasketing barriers 50 may improve the comfort of the user. For example, as described above, the absorbent article 10 includes one or more elastics 34 in each standing leg cuff 28. The elastics 34 are tensioned to allow the standing leg cuffs 28 to contact the skin of a user. The elastics 34 thus need to be tensioned such that a sufficient pressure is applied to the skin of the user to prevent leakage through the sides of the absorbent article 10. Such applied pressure often results in irritation of the user's skin, resulting in red markings and rashes.

The cuff web 32 and the gasketing barriers 50 may be made of different materials. For example, referring to FIGS. 4 and 12, the standing leg cuffs 28 include the gasketing barriers 50 and the cuff webs 32. As shown, the cuff webs 32 are formed of a different material than the gasketing barriers 50. As noted above, the gasketing barriers 50 may be formed of a soft and lofty nonwoven material. In some embodiments, the gasketing barriers 50 may be formed of a carded web nonwoven while the cuff webs 32 may be formed of a spunbond-meltblown-spunbond nonwoven. For example, the gasketing barriers 50 may be formed of a bicomponent fiber carded nonwoven. An advantage of this material is that the biocomponent fibers provide increased softness while also containing polypropylene for increased strength. Accordingly, the comfort of the user may be improved while also providing a denser fiber structure, which may improve the leakage protection of the standing leg cuffs 28. In some embodiments, one or both of the gasketing barrier 50 and the cuff web 32 may be at least partially sustainable. For example, the material may include cotton.

In some embodiments, the cuff web 32 and the gasketing barrier 50 may be formed of materials with different basis weights. For example, the cuff web 32 may be made of a material with a basis weight of about 20 to about 25 gsm. The gasketing barrier 50 may be made of a material with a basis weight of about 10 to about 15 gsm. Accordingly, the cuff web 32 and the gasketing barrier 50 may form a laminate. The basis weight of the laminate may be in the range of about 10 to about 25 gsm.

The material used to form the gasketing barriers 50 may be softer than the material used to form the cuff webs 32. This design may improve the comfort of the user while also improving the leakage protection of the standing leg cuffs 28. For example, the softness of materials used herein may be determined through tests performed by SGS, such as by one or more of the TS7 test, the TS750 test, and/or the SGS softness index. Exemplary Softness Index values for different nonwovens may be found in the table below:

| SGS # | Basis Wt. (gsm) | Manufacturer | Nonwoven Description | Softness Index |
|---|---|---|---|---|
| 1750 | 13.5 | Berry | Standard SMS | 56 |
| 1764 | 18.0 | Shalag | Carded Bi-Co Web (ST61ETH18) | 88 |
| 1765 | 13.5 | Berry | SSMMS Kamisoft (with soft additive) | 61 |
| 1766 | 17.0 | Berry | STNC (KS-VM/PV) | 64 |
| 1767 | 35.0 | Berry | SSMMS Kamisoft | 65 |
| 1768 | 35.0 | Berry | APEX High Loft Nonwoven | 74 |

Figure 12:
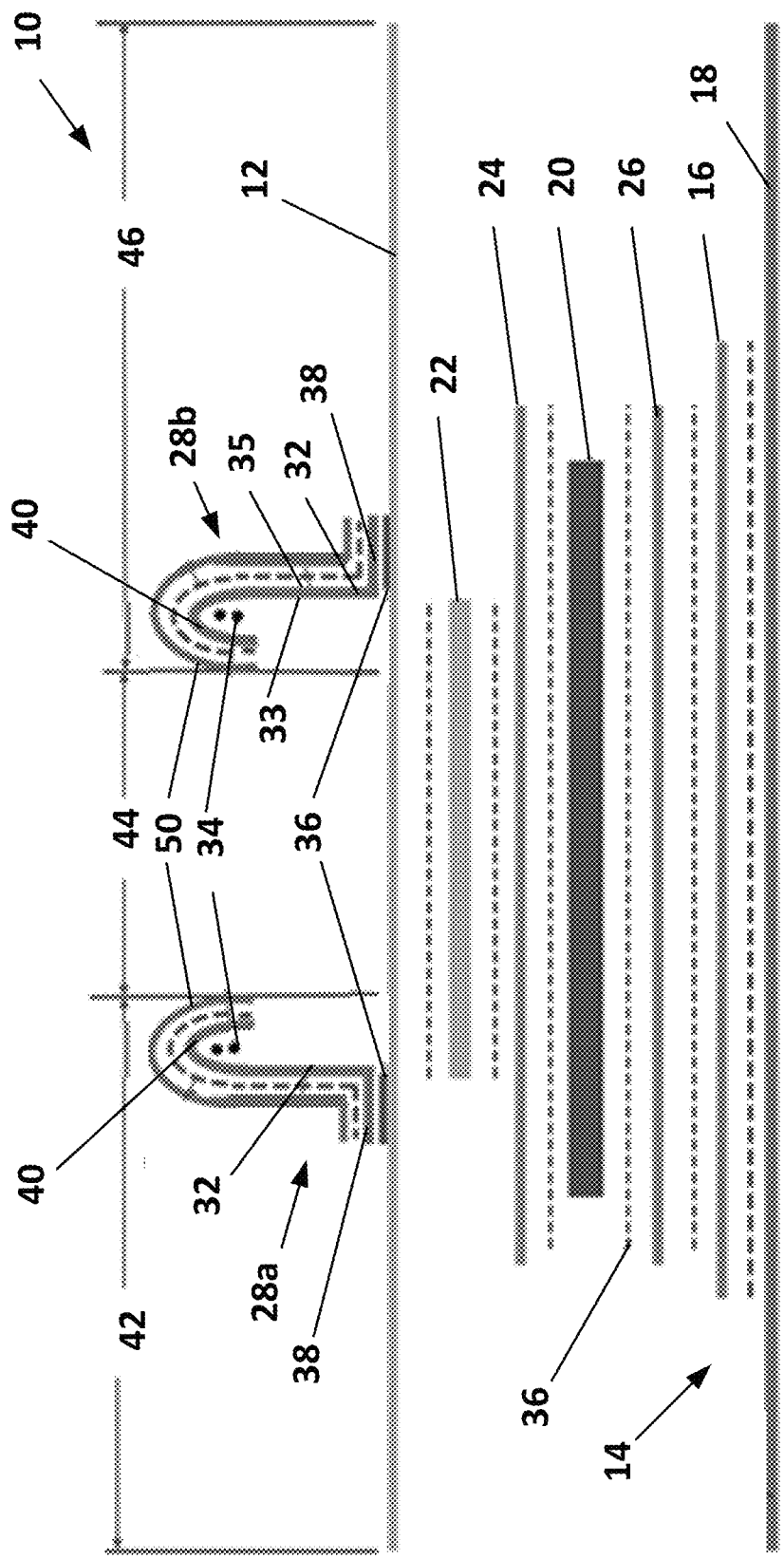
FIG. 12 shows a cross-sectional view of a disposable absorbent article having a gasketing barrier in accordance with another example embodiment.

The positioning of the gasketing barriers 50 on the standing leg cuffs 28 may vary. In some embodiments, the gasketing barriers 50 may cover one side of the cuff web 32. As exemplified in FIG. 12, the cuff web 32 has a first side 33 and an opposed second side 35, each extending between the base 38 and the top 40 of the cuff web 32. As shown, the gasketing barrier 50 is coupled to the second side 35 of the cuff web 32. The gasketing barrier 50 may cover the entire length of the cuff web 32, extending from the base 38 to the top 40 as shown in FIG. 12, or may cover only a portion of the cuff web 32.

Figure 4:
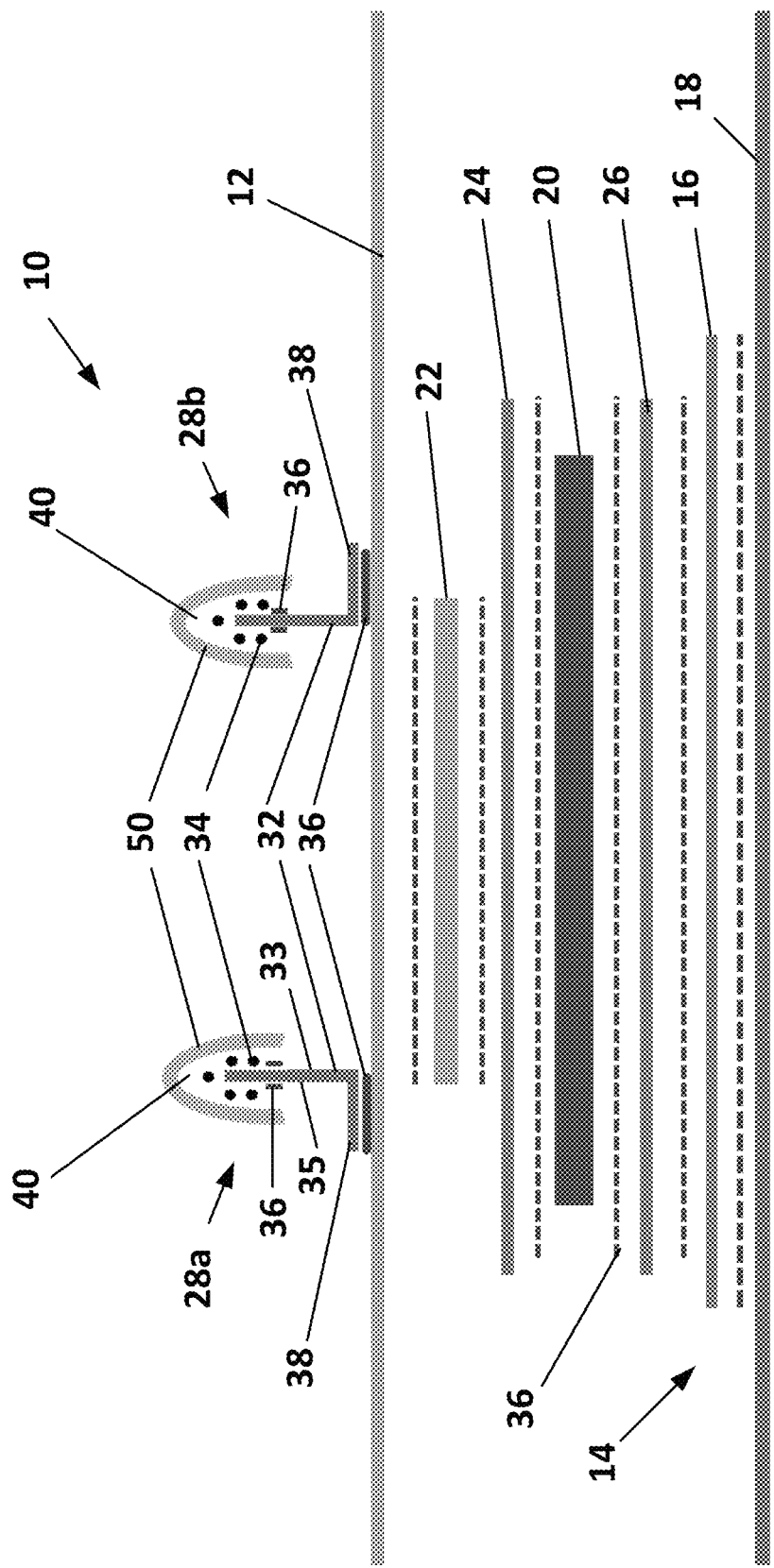
FIG. 4 shows a cross-sectional view of the disposable absorbent article of FIG. 3 along the line B-B.

In some embodiments, the gasketing barriers 50 may cover at least a portion of each side of the cuff web 32. For example, as shown in FIG. 4, the gasketing barriers 50 cover the top 40 of the cuff web 32, partially covering the first side 33 and the second side 35 of the cuff web 32.

In some embodiments, the elastics 34 of each standing leg cuff 28 may be covered by the gasketing barriers 50. The gasketing barriers 50 may therefore provide a robust and soft gasketing means, reducing corrugations or micro-gaps along the top edge of the standing leg cuffs 28. Positioning the gasketing barriers 50 along the top 40 of the standing leg cuffs 28 and over one or more elastics 34 may help prevent fluid leakage while providing a softer gasketing means against the body.

Figure 11:
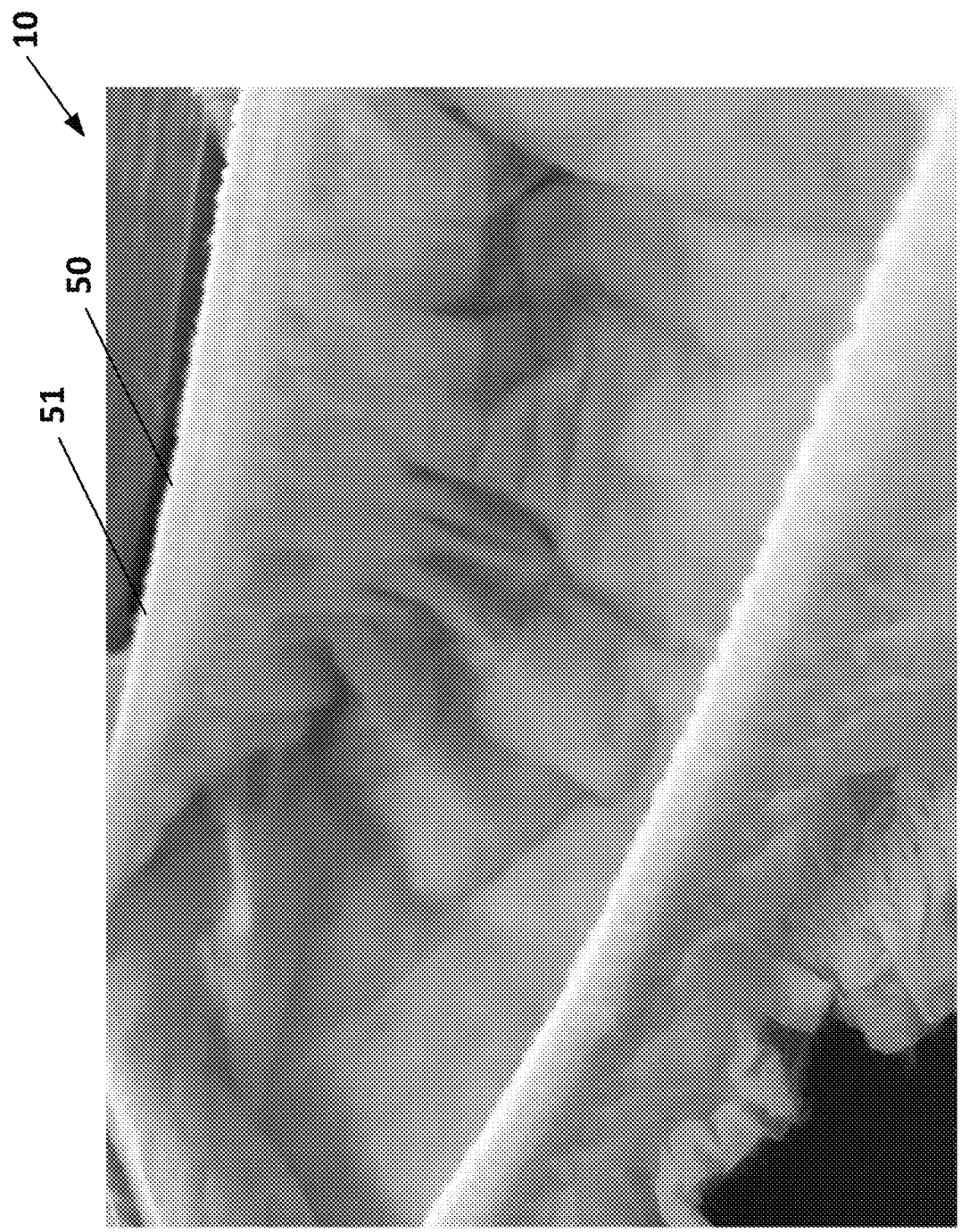
FIG. 11 shows an image of a disposable absorbent article having a gasketing barrier in accordance with another example embodiment.

For example, referring to FIG. 11, shown therein is an image of the article 10 with gasketing barriers 50. As shown in the image, the gasketing barriers 50 cover the top 40 of the standing leg cuffs 28, providing a soft barrier for the user's skin. As shown, the gasketing barriers 50 form folds 51 that are generally transverse to the length of the standing leg cuffs 28. The folds 51 are also generally evenly spaced from one another. Having a generally consistent texture of folds 51 for the gasketing barriers 50 may improve the comfort of the user by allowing for a more even pressure to be applied to the user's skin.

In some embodiments, the softened contact between the standing leg cuffs 28 and the skin of the user may allow for the tension of the elastics 34 to be increased. Increasing the tension of the elastics 34 may reduce leakage at the standing leg cuffs 28. However, retracting the elastics 34 at higher tensions may result in a scratchy/rough feeling for the user of the article 10. The scratchy/rough feeling is caused by a reduction in the thickness of the nonwoven material between the elastic 34 and the user's skin due to the increased tension of the elastic 34. The nonwoven material typically acts as a buffer to protect the skin from the elastic material under tension. Thus, a higher quantity of soft nonwoven material reduces the likelihood of skin irritation. The loftiness and softness of the gasketing barriers 50 may provide a more cushioned and smoother material in direct contact with the body, thereby improving the comfort and skin wellness of the user. The combination of a softer material at higher tension may therefore provide for reduced leakage without compromising the comfort of the user.

In some embodiments, the soft and lofty nonwoven used in the gasketing barriers 50 may also be hydrophobic. For example, the gasketing barriers 50 may include small denier fibers. When compressed together with elastic, denier fibers may create a thicker and higher density elastic composite. This composite may create a more robust and effective fluid barrier. The small denier fibers may include a blend of materials such as bicomponent fibers. The bicomponent fibers may include a polyethylene sheath and polypropylene core, polyethylene sheath and polyester core, or polypropylene sheath and polyester core.

The soft gasketing barriers 50 may be used in additional locations on the article 10. For example, the gasketing barriers 50 may be used along the edges of the front and/or back waist openings of the absorbent article 10. Traditional absorbent products, such as pants or underwear, contain waistbands where the phobic nonwoven materials of the product chassis are folded over, from outside to inside, over the elastic material(s). This process creates the front and back waist openings of the product. By including the gasketing barriers 50 on the front and/or back waist openings, the comfort and leakage of the article may be improved. In some embodiments, the gasketing barriers 50 may be used in both the standing leg cuffs 28 and along the front and back waist openings of the absorbent article 10. The gasketing barriers 50 may also be added to leakage barrier flaps and/or fecal containment pockets, which are intended to keep urine and/or feces from leaking out the back and/or waist area of the product. These leakage barriers flaps are usually positioned in the cross-direction of the product, which is perpendicular to the front and back edges of the absorbent core.

The use of the gasketing barriers 50 described herein may also reduce the cost of improving the comfort and leakage of the absorbent article 10. For example, traditional standing leg cuffs that are attached to absorbent articles often include elastic material(s) that are positioned between two thin layers of phobic nonwoven materials. The standing leg cuffs typically include one layer of phobic nonwoven material that is folded upon itself over the elastic material(s). If the thin layers of phobic nonwoven material were all replaced with a thicker, phobic, nonwoven material, the cost of the article would increase. However, by merely replacing the top portion of the standing leg cuffs with a thick, phobic, nonwoven material, the rest of the thin layers of nonwoven material may remain the same. Therefore, the comfort and leakage of the article may be improved without significantly affecting the cost of the article.

Similarly, the use of the gasketing barriers 50 on the front and back waist openings may improve the comfort and leakage of the article without significantly affecting the cost. If this thinner layer of phobic nonwoven material at the front and back waist openings were replaced with a thicker layer of phobic nonwoven material, the cost of the product would increase due to the much larger surface area of the front and back chassis of the article compared to the standing leg cuffs. However, merely replacing the waistband area of the product chassis with a thicker layer of phobic nonwoven material reduces the cost of improving the leakage and comfort of the article.

The improved fluid containment and comfort features described above may be used in a variety of different absorbent products, such as, for example, training pants, baby diapers, adult diapers, adult pants, youth pants, incontinence pads, incontinence male guards, wound care, feminine hygiene articles, etc.

Referring to FIGS. 3-7, shown therein are example embodiments of an article 10 with gasketing barriers 50. As shown more clearly in FIGS. 4 and 7, the standing leg cuffs 28 are coupled to the topsheet 12 by bond 36. Joining the standing leg cuffs 28 to the topsheet 12 in this manner allows for a simplified construction of the article 10. For example, the standing leg cuffs 28 may first be assembled separately from the rest of the article 10 and then may be easily attached to the topsheet 12.

Referring to FIGS. 5A-5F, shown therein is an example process for manufacturing the standing leg cuffs 28. As shown in FIGS. 5A and 5B, elastics 34 may be coupled to the gasketing barrier 50. In some embodiments, a second gasketing barrier 50b may be applied on top of the elastics 34 and the first gasketing barrier 50a. The two gasketing barriers 50 may be used to sandwich the elastics 34 and secure them in place before folding, as shown in FIG. 5C. Each of the first and second gasketing barriers 50 may be formed of the same or different materials. For example, in some embodiments, the first gasketing barrier 50a, which is coupled to the cuff web 32, may be made of a lighter weight nonwoven material that is less soft and less lofty as compared to the second gasketing barrier 50b. The first gasketing barrier 50a may be formed of a lighter weight nonwoven without reducing the comfort to the user because the first gasketing barrier 50a may not contact the skin of the user and may mainly be used as a carrier for the elastics 34.

The elastics 34 may be coupled to the gasketing barriers 50 by any means known in the art, such as by an adhesive, mechanical fastening, or ultrasonic bond. For simplicity, the bonds for the elastics 34 are omitted from the figures. Once the elastics 34 are coupled to the gasketing barriers 50, the assembled gasketing barriers 50 are then coupled to the cuff web 32 to form the standing leg cuff 28, as shown in FIGS. 5D and 5E. In the example embodiment, the gasketing barrier 50 is coupled to the cuff web 32 by adhesive bonds 36. Once the standing leg cuff 28 is assembled, it may then be coupled to the top sheet 12, as shown in FIG. 5F.

Figure 6A:
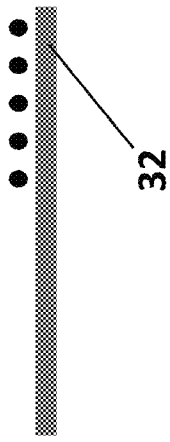
FIGS. 6A-6D show a process for assembling a standing leg cuff on the disposable absorbent article of FIG. 4 in accordance with another example embodiment.
Figure 6B:
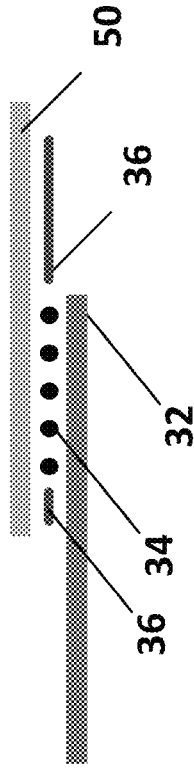
Figure 6C:
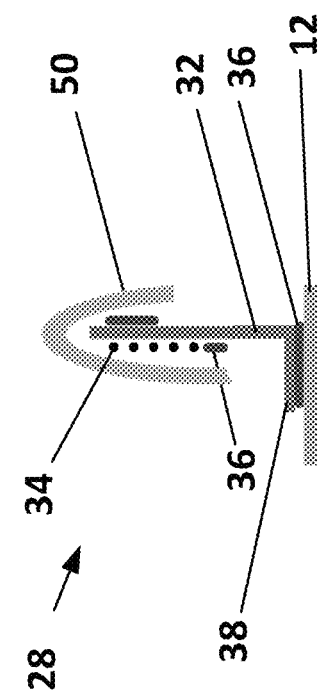
Figure 6D:
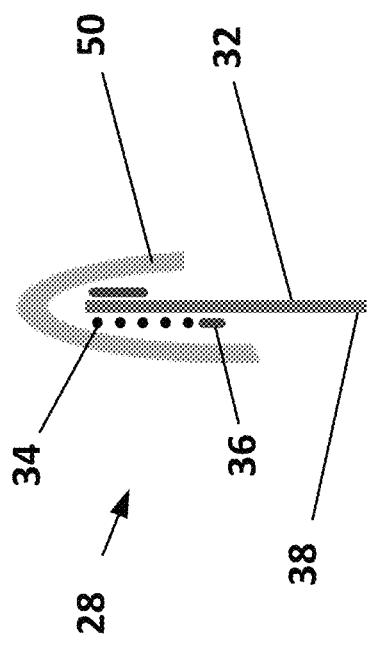

Alternatively, in some embodiments, the elastics 34 may first be coupled to the cuff web 32. In such embodiments, the standing leg cuff 28 may have a single gasketing barrier 50 since the elastics 34 may be supported on one side by the cuff web 32 and on the other side by the gasketing barrier 50. For example, referring to FIGS. 6A-6D, shown therein is an example process for manufacturing the standing leg cuffs 28. As shown in FIG. 6A, the elastics 34 are first coupled to the cuff web 32. As described above, the bonds securing the elastics 34 are omitted from the figures for simplicity. Once the elastics 34 are coupled to the cuff web 32, the gasketing barrier 50 may be positioned over the elastics 34 such that a portion of the gasketing barrier 50 extends past the end of the cuff web 32, producing some overlap, as shown in FIG. 6B. The overlapping portion of the gasketing barrier 50 may then be folded and adhered to the cuff web 32, as shown in FIG. 6C. Once the gasketing barrier 50 is coupled to the cuff web 32, the entire standing leg cuff 28 may be coupled to the topsheet 12, as shown in FIG. 6D.

The elastics 34 may be positioned in the standing leg cuffs 28 in any location that allows the standing leg cuffs 28 to form a barrier adjacent to the topsheet 12. Referring to FIG. 4, shown therein is a cross-sectional view of the disposable absorbent article 10, focusing on the crotch area of the article 10. In some embodiments, as described above, the elastics 34 may be coupled between two gasketing barriers 50a and 50b before forming the standing leg cuffs 28. For simplicity, FIG. 4 illustrates a single layer of gasketing barrier 50. As shown in the example embodiment, the elastics 34 are elongated and coupled to the gasketing barriers 50. The gasketing barriers 50 are folded over and coupled to the cuff web 32.

Figure 7:
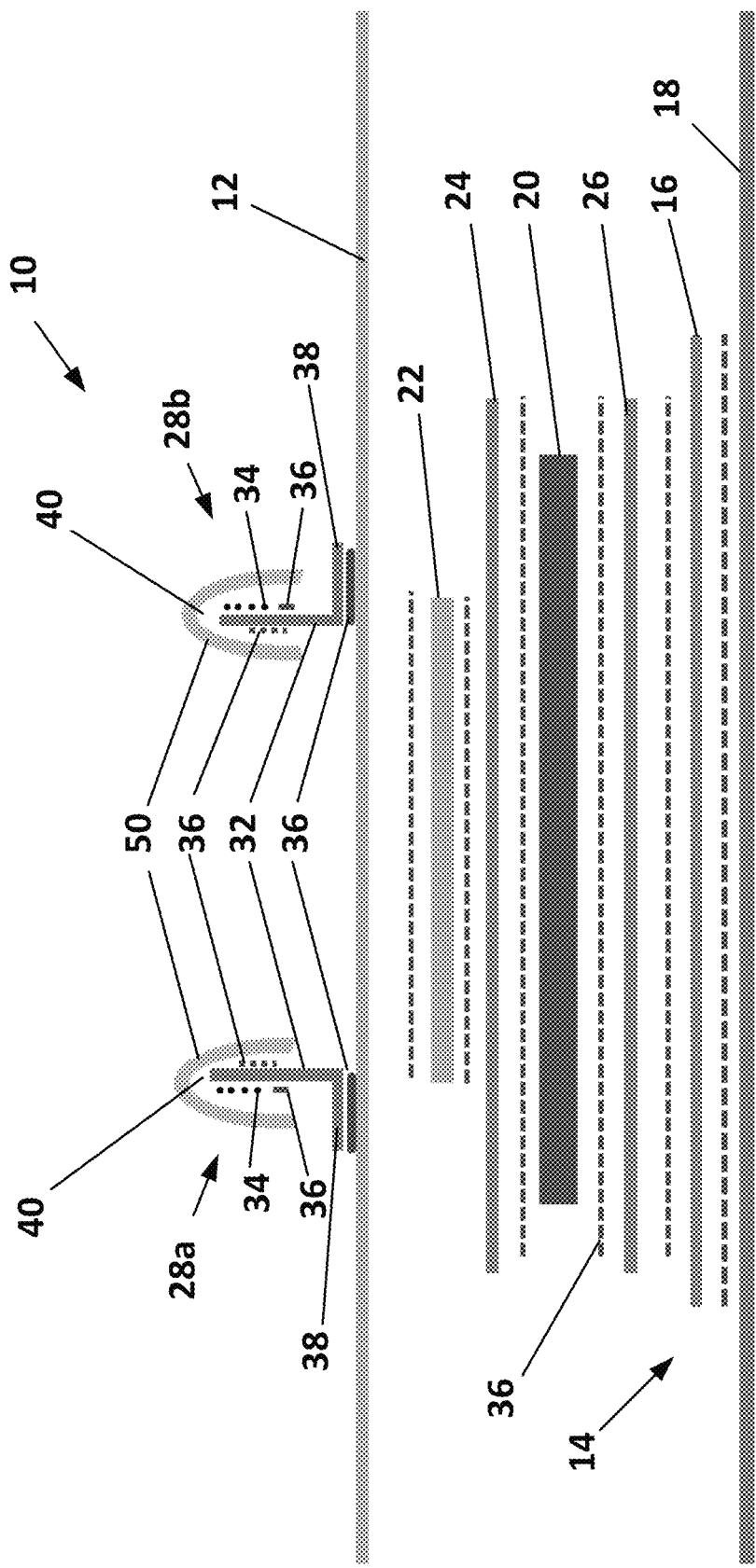
FIG. 7 shows a cross-sectional view of a disposable absorbent article having a gasketing barrier in accordance with another example embodiment.

Referring now to FIG. 7, shown therein is a cross-sectional view of an example embodiment of an article 10, manufactured using the process of manufacturing the standing leg cuff 28 in FIGS. 6A-6D, wherein the elastics 34 may be coupled to one side of the gasketing barriers 50. The gasketing barriers 50 may then be coupled to the cuff web 32. Positioning the elastics 34 on one side of the standing leg cuffs 28 may improve the speed of manufacturing the article 10 since only one set of elastics 34 needs to be properly positioned before securing the elastics 34 to the standing leg cuffs 28.

Figure 8:
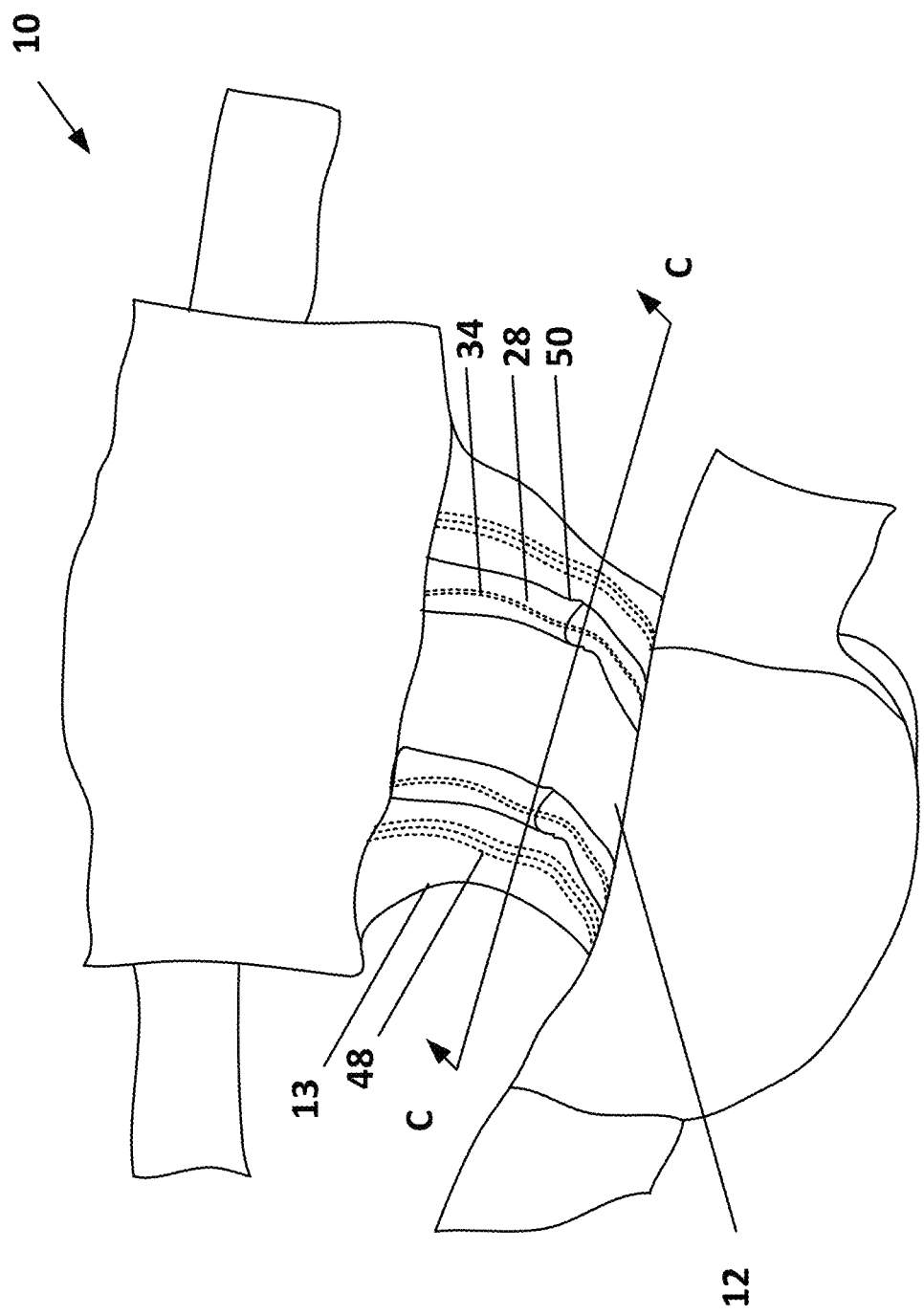
FIG. 8 shows a perspective view of a disposable absorbent article having a gasketing barrier in accordance with another example embodiment
Figure 9:
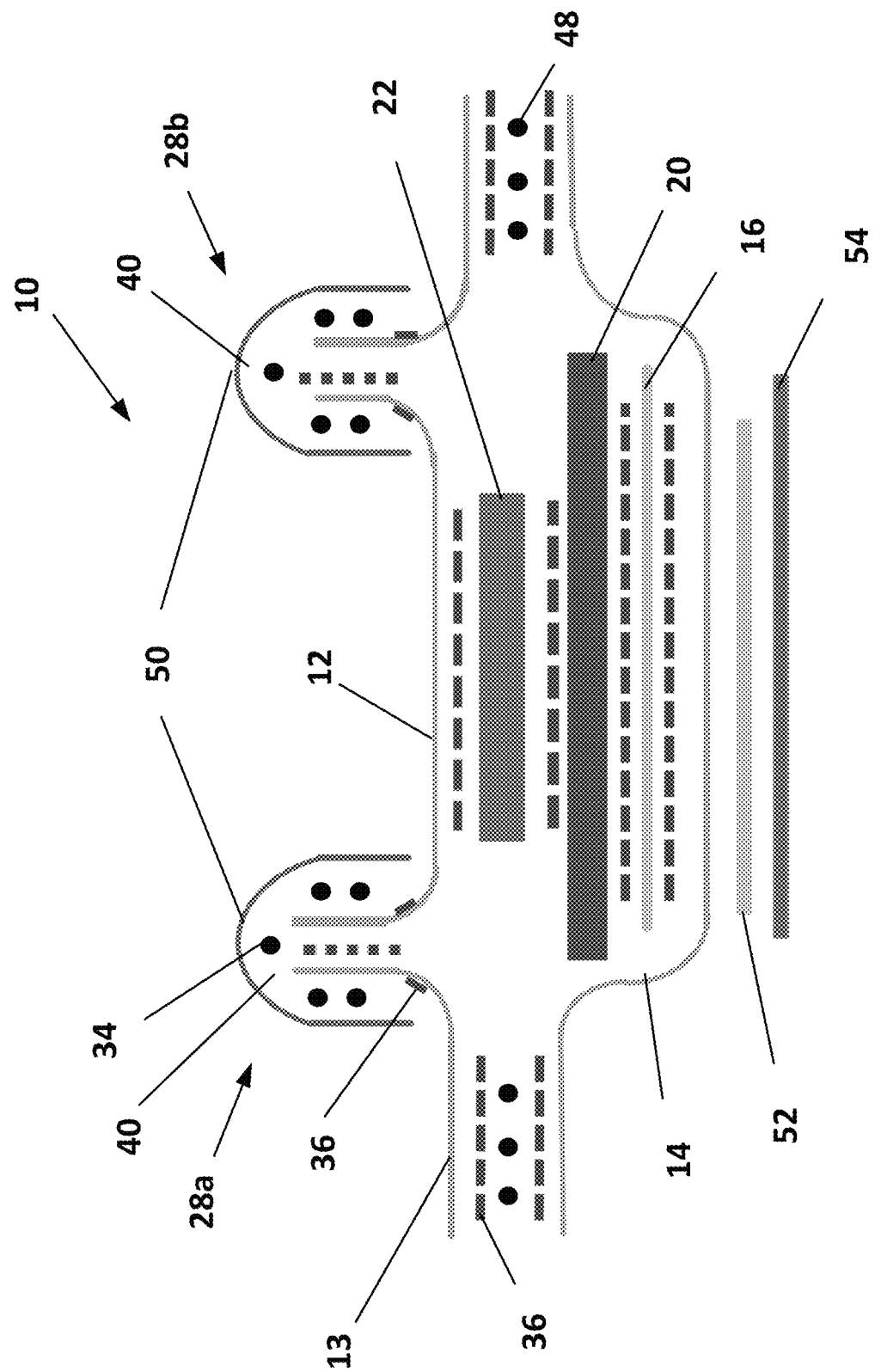
FIG. 9 shows a cross-sectional view of the disposable absorbent article of FIG. 8 along the line C-C.
Figure 10:
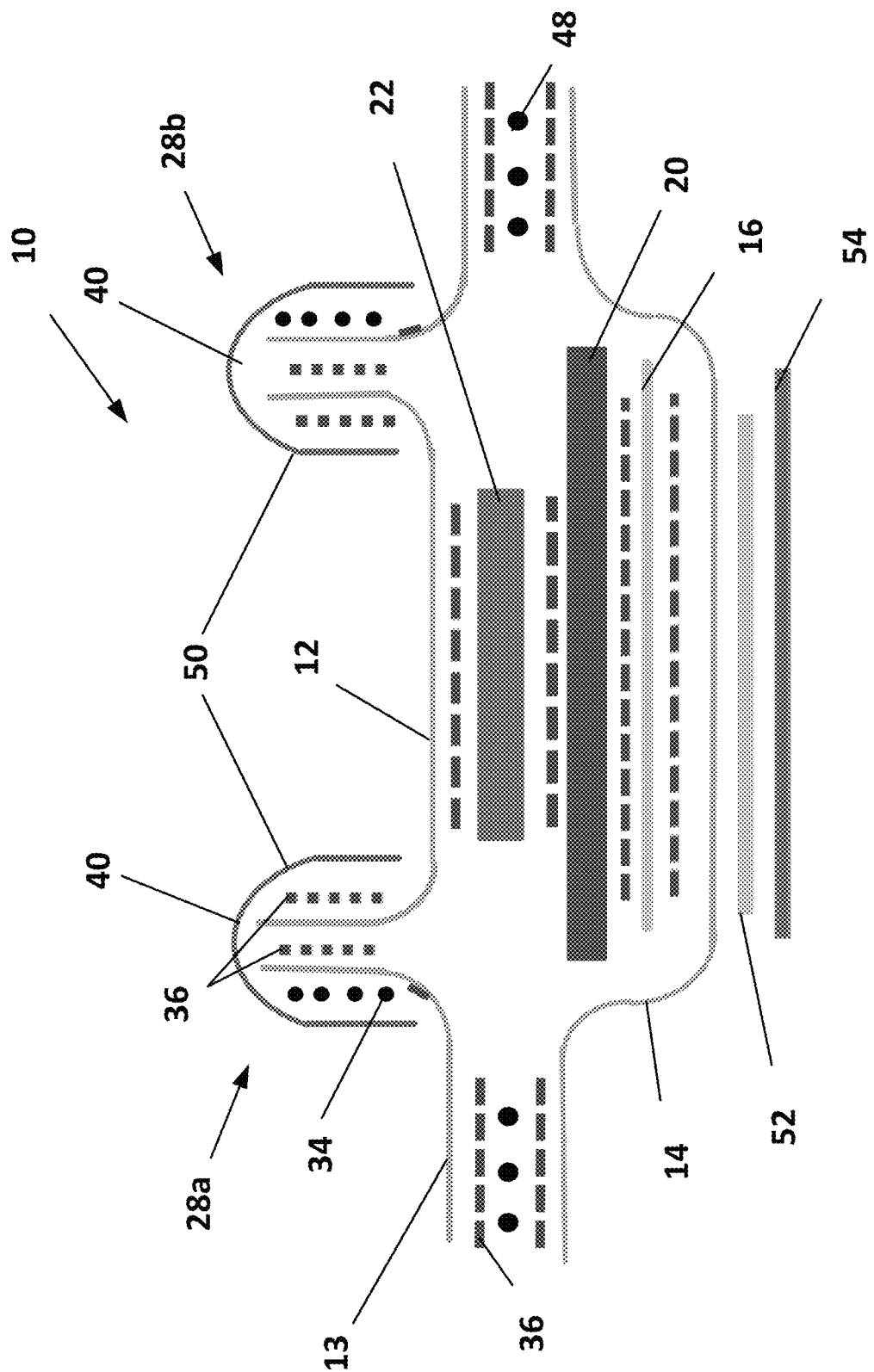
FIG. 10 shows a cross-sectional view of a disposable absorbent article having a gasketing barrier in accordance with another example embodiment.

Referring to FIGS. 8-10, shown therein are example embodiments of an absorbent article 10 of alternative construction. The article 10 includes first and second side sheets 13a, 13b, together referred to as side sheets 13. The side sheets 13 are coupled to the backsheet 14. The side sheets 13 may be a nonwoven material. In this example embodiment, the gasketing barriers 50 may encompass the elastics 34 and may be coupled to one or more of the standing leg cuffs 28 and the topsheet 12. Thus, the top layer of the article 10 is formed of three sheets, rather than a single top sheet 12 as shown in FIGS. 3-7.

The intersection between the side sheets 13 and the top sheet 12 may be used to form the standing leg cuffs 28. In the example embodiment shown in FIGS. 8-10, the standing leg cuffs 28 are formed by coupling the side sheets 13 to the topsheet 12. Next, one or more elastics 34 are coupled to the inside of each gasketing barrier 50. The gasketing barrier 50 may then be coupled to both the topsheet 12 and the side sheet 13, thereby covering the joined region between the two sheets. Alternatively, the elastics 34 may be coupled to the joined region between the topsheet 12 and the side sheet 13.

The gasketing barrier 50 may then be placed over the elastics 34 and coupled to the topsheet 12 and the side sheet 13.

Forming the article 10 with side sheets 13 may allow for the use of different materials for the baby side of the article 10. For example, the side sheets 13 may be a hydrophobic material and the topsheet 12 may be a hydrophilic material. Using different materials for the side sheets 13 and the topsheet 12 may improve the transmission of fluids from the topsheet 12 to the absorbent core 20 without treating the topsheet 12 with a surfactant and without processing the topsheet 12 to have pores and/or apertures. Additionally, having hydrophobic side sheets 13 may improve the leakage of the article 10 by reducing the likelihood that liquid will travel past the peripheral edges of the topsheet 12.

In some embodiments, as shown in the example embodiments of FIGS. 8-10, one or more elastics 48 may be disposed between the side sheets 13 and the backsheet 14 to provide elastic retraction to the sides of the article 10. The standing leg cuffs 28 provide the first barrier and the side elastics 34 provide a second barrier, thereby improving the leakage protection of the article 10.

In some embodiments, adding additional elastics 34 and 48 to the article 10 may improve the comfort of the user. For example, by increasing the number of elastics 34 and/or 48, the tension of the elastics may be reduced, while maintaining a similar level of leakage protection. Reducing the tension of the elastics 34 and 48 also reduces the pressure the elastics apply on the skin of the user, thereby improving the comfort of the user.

In some embodiments, the elastics 34 and/or 48 may be differentially tensioned. For example, referring to FIG. 4, the elastic 34 proximate the top 40 of the standing leg cuff 28 may have a lower tension than the remaining four elastics 34 distal to the top 40. Reducing the pressure along the top 40 of the standing leg cuffs 28 may improve the comfort of the user, while maintaining a higher pressure along the remaining elastics 34 to ensure that the leakage protection is not reduced. In some embodiments, each of the elastics 34 may be differently tensioned.

In some embodiments, the standing leg cuffs 28 may have elastics 34 of varying lengths along different portions of the standing leg cuffs 28. For example, referring again to FIG. 4, the elastic 34 proximate to the top 40 of the standing leg cuff 28 may be shorter than the remaining four elastics 34. Decreasing the length of the elastic 34 may reduce the costs of manufacturing the article 10. Shortening the elastic 34 proximate the top 40 may also improve the comfort of the user by allowing for reduced tension due to the decrease in elasticity in the waist regions of the article 10.

The comfort of the user may also be improved by increasing the surface area of the gasketing barriers 50. As described above, the gasketing barriers 50 may be coupled at or near the top 40 of the standing leg cuffs 28 to improve the leakage and comfort of the diaper 10, as shown in the example embodiments of FIGS. 3-7. In some embodiments, the gasketing barriers 50 may be coupled to or near the base 38 of the standing leg cuffs 28. For example, referring to FIGS. 8-10, each gasketing barrier 50 is coupled to each of the side sheet 13 and the topsheet 12, near the base 38 of the standing leg cuff 28. Coupling the gasketing barriers 50 at or near the base 38 of the standing leg cuffs 28 increases the surface area of the gasketing barriers 50, thereby improving the comfort of the user. The increased surface area of the gasketing barriers 50 may help reduce red marks caused by the elastics 34 on the skin of the user.

In some embodiments, as exemplified in FIGS. 9-10, the article 10 may include positioning adhesive 52 and release paper 54. The release paper 54 prevents the adhesive 52 from adhering to other surfaces before its use. The positioning adhesive 52 may be used to adhere the article 10 to a user's garment to prevent the article 10 from moving from its desired position. To use the positioning adhesive 52 a user must first remove the release paper 54 and then place the positioning adhesive 52 against the garment.

One type of material that can be used for the soft gasketing barriers 50 is a soft hydrophobic nonwoven. For example, in one embodiment, the soft gasketing barrier 50 may be formed with a soft nonwoven material having a basis weight of 18 gsm, identified as ST61ETH18, available from Shalag Nonwovens located in Oxford, North Carolina. Other materials and basis weights can be used. This includes through-air-bonded nonwovens, spunlaced nonwovens, carded nonwovens, laminated nonwovens, soft spunbond nonwovens, etc. The nonwoven basis weight can range from 15 to 125 gsm. For example, one type of material that can be used as the gasketing barrier is a hydrophobic carded nonwoven from TWE (Para Therm Loft 469) with a basis weight of about 22 gsm.

One type of material that can be used as the cuff web 32 is a thin hydrophobic nonwoven, comprising of SMS (Spunbond-Meltblown-Spunbond), with a basis weight of about 13.5 gsm, available from Berry Global located in Charlotte, North Carolina. Other materials and basis weights can be used. This includes poly films, poly film & nonwoven laminates, extruded poly & nonwoven laminates, breathable films, breathable poly laminates, etc. In some embodiments, the SMS nonwoven may provide a hydro-head of at least 15 mBar.

One type of material that can be used as the elastic strand 34 is a synthetic spandex thread identified as 800 dTex available from Hyosung located in Seoul, South Korea.

One type of material that can be used to adhere the elastic strand 34 to the soft gasketing barriers 50 is an elastic hot melt adhesive identified as H4356 available from Bostik Corporation located in Wauwatosa, WI.

One type of material that can be used to adhere the standing leg cuffs 28 to the topsheet 12 is a construction hot melt adhesive identified as H4384 available from Bostik Corporation located in Wauwatosa, WI.

One type of absorbent core 20 that can be used is a mixture of cellulose pulp and super absorbent polymer that is wrapped in top nonwoven 24 and bottom nonwoven 26. One type of cellulose pulp that can be used is soft-pine ECF pulp available from Domtar located in Fort Mill, South Carolina. One type of superabsorbent polymer that can be used is identified as Aquakeep HP650 available from Sumitomo Seika Chemicals Company located in Osaka, Japan. One type of nonwoven wrap that can be used is a 10 gsm hydrophilic nonwoven available from Berry Global located in Charlotte, North Carolina.

One type of material that can be used as the acquisition distribution layer 22 is hydrophilic high-loft nonwoven identified as ST6PERH50 from Shalag Nonwovens located in Oxford, North Carolina.

One type of material that can be used as the poly barrier 16 is a 0.65 mil polyethylene film available from Berry Global located in Charlotte, North Carolina.

One type of material that can be used as the topsheet 12 is a 15 gsm zone-coated nonwoven available from Berry Global located in Charlotte, North Carolina.

On type of material that can be used as the side nonwoven 13 for pad-like products is a 15 gsm hydrophobic nonwoven from Berry Global located in Charlotte, North Carolina.

One type of material that can be used as the backsheet 14 is 13.5 gsm soft hydrophobic nonwoven available from Fitesa located in Simpsonville, South Carolina.

One type of material that can be used as the backsheet 14 is a 0.55 mil polypropylene and polyethylene film available from Berry Global located in Charlotte, North Carolina.

One type of material that can be used as the backsheet 14 is a breathable poly laminate identified as XC3-121-2477 available from Berry Plastics located in Charlotte, North Carolina.

One type of material that can be used as the positioning adhesive 52 is a hot melt adhesive identified as NW1043 available from H.B. Fuller Corporation located in St. Paul, Minnesota.

One type of material that can be used as the release paper 54 is a 32 gsm silicone-coated printed paper available from Mondi Group located in Pleasant Prairie, Wisconsin.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims is not limited to the examples set out herein, but should be understood in a manner consistent with the description as a whole.

We claim:

1. An absorbent article having a front edge, a back edge, and two longitudinally extending side edges, the absorbent article comprising:
    a topsheet, the topsheet being liquid pervious;
    a backsheet coupled to the topsheet, the backsheet being liquid impervious;
    an absorbent core disposed between the topsheet and backsheet, the absorbent core containing at least one absorbent material;
    an acquisition distribution layer disposed between a bottom side of the topsheet and a top side of the absorbent core; and
    first and second standing leg cuffs, each standing leg cuff includes:
        a cuff web having a base, a top, and a first side and an opposed second side extending between the base and the top, the base coupled to the topsheet;
        one or more elastics coupled adjacent to the top of the cuff web;
        a gasketing barrier coupled to the second side of the cuff web, wherein the cuff web is made of a first material, the gasketing barrier is made of a second material, and the first material is different than the second material,
    wherein each gasketing barrier surrounds the top of the corresponding cuff web.

2. The absorbent article of claim 1, wherein the second material is softer than the first material as measured by any one of the SGS TS7 test and the SGS TS750 test.

3. The absorbent article of claim 1, wherein the second material is softer than the first material as measured by the SGS softness index.

4. The absorbent article of claim 1, wherein the gasketing barrier extends from the base to the top of the cuff web.

5. The absorbent article of claim 1, wherein the top of the cuff web comprises a folded portion, the folded portion for covering the one or more elastics.

6. The absorbent article of claim 1, wherein the first material has a basis weight of about 13.5 gsm.

7. The absorbent article of claim 6, wherein the second material has a basis weight of about 22 gsm.

8. The absorbent article of claim 1, wherein the second material has a basis weight of about 22 gsm.

9. The absorbent article of claim 1, wherein the first material has a basis weight in the range of about 10 gsm to about 15 gsm.

10. The absorbent article of claim 1, wherein the second material has a basis weight in the range of about 20 gsm to about 25 gsm.

11. The absorbent article of claim 1, wherein in each standing leg cuff, the elastics are tensioned to lift the top of the standing leg cuff.

12. The absorbent article of claim 1, wherein the bases of the standing leg cuffs are coupled to the topsheet with at least one of an adhesive and ultrasonic bonding.

13. The absorbent article of claim 1, wherein each gasketing barrier is coupled to each cuff web by at least one of an adhesive and ultrasonic bonding.

14. The absorbent article of claim 1, wherein at least one of the cuff web and the gasketing barrier comprises at least one of a hydrophobic spunbond-meltblown-spunbond nonwoven, a poly film, a breathable film, a poly laminate, a carded web nonwoven, a through-air carded nonwoven, and a hydrophobic spunlaced nonwoven.

15. The absorbent article of claim 14, wherein the cuff web comprises a spunbond-meltblown-spunbond nonwoven and the gasketing barrier comprises a carded web nonwoven.

16. The absorbent article of claim 15, wherein the carded web comprises bicomponent fibers and polypropylene.

17. An absorbent article having a front edge, a back edge, and two longitudinally extending side edges, the absorbent article comprising:
    a topsheet, the topsheet being liquid pervious;
    a backsheet coupled to the topsheet, the backsheet being liquid impervious;
    an absorbent core disposed between the topsheet and backsheet, the absorbent core containing at least one absorbent material;
    an acquisition distribution layer disposed between a bottom side of the topsheet and a top side of the absorbent core; and
    first and second standing leg cuffs, each standing leg cuff assembled with a transverse outboard portion of the topsheet and a transverse inboard portion of a side sheet, each standing leg cuff includes:
        a cuff web having a base, a top, and a first side and an opposed second side extending between the base and the top;
        one or more elastics coupled adjacent to the top of the cuff web;
        a gasketing barrier coupled to the second side of the cuff web, wherein the cuff web is made of a first material, the gasketing barrier is made of a second material, and the first material is different than the second material,
    wherein each gasketing barrier surrounds the top of the corresponding cuff web.

18. The absorbent article of claim 17, wherein at least some of the elastics are positioned between the transverse outboard portion of the topsheet and the transverse inboard portion of the side sheet.

* * * * *